United States Patent
Wang et al.

(10) Patent No.: US 11,684,893 B2
(45) Date of Patent: Jun. 27, 2023

(54) METHOD FOR EXOSOME SEPARATION AND EXTRACTION BY STACKED CENTRIFUGAL FILTRATION

(71) Applicant: Guangzhou Supbio Bio-technology and Science Co., Ltd., Guangdong (CN)

(72) Inventors: Tong Wang, Guangdong (CN); Yizhi Cui, Guangdong (CN); Yanzhang Luo, Guangdong (CN); Jiahui Guo, Guangdong (CN)

(73) Assignee: Guangzhou Supbio Bio-technology and Science Co., Ltd., Guangdong (CN)

( * ) Notice: Subject to any disclaimer, the term of this patent is extended or adjusted under 35 U.S.C. 154(b) by 1194 days.

(21) Appl. No.: 16/307,354

(22) PCT Filed: Aug. 31, 2016

(86) PCT No.: PCT/CN2016/097562
§ 371 (c)(1),
(2) Date: Dec. 5, 2018

(87) PCT Pub. No.: WO2018/018707
PCT Pub. Date: Feb. 1, 2018

(65) Prior Publication Data
US 2019/0134565 A1     May 9, 2019

(30) Foreign Application Priority Data

Jul. 26, 2016 (CN) .......................... 201610595164.2

(51) Int. Cl.
*B01D 61/18*      (2006.01)
*B01L 3/00*       (2006.01)
(Continued)

(52) U.S. Cl.
CPC ............ *B01D 61/18* (2013.01); *B01D 61/145* (2013.01); *B01D 61/146* (2022.08); *B01D 63/06* (2013.01);
(Continued)

(58) Field of Classification Search
CPC ...... B01D 61/18; B01D 35/30; B01D 35/301; B01D 35/34
See application file for complete search history.

(56) References Cited

U.S. PATENT DOCUMENTS

| 3,583,627 A | 6/1971 | Wilson |
| 5,647,990 A | 7/1997 | Vassarotti |

(Continued)

FOREIGN PATENT DOCUMENTS

| CN | 101993472 A | 3/2011 |
| CN | 102782472 A | 11/2012 |

(Continued)

OTHER PUBLICATIONS

Japan Patent Office, Notice of Reasons for Refusal for corresponding JP Application No. 2019-523151, dated Jan. 7, 2020, 6 pages, English translation attached.

(Continued)

*Primary Examiner* — Ryan B Huang
(74) *Attorney, Agent, or Firm* — Christopher & Weisberg, P.A.

(57) ABSTRACT

A method for exosome separation and extraction by stacked centrifugal filtration. It is used in molecular biology and clinical examination and comprises an exosome separation and extraction kit consisting of the stacked centrifugal filtration device, an incubation buffer and a protease K. The sample to be tested is incubated at room temperature using the incubation buffer and an appropriate amount of protease K, followed by centrifugation in a centrifuge matching the (Continued)

stacked centrifugal filtration device. After mixing thoroughly, the retained liquid in the ultrafiltration tube is collected to obtain the exosomes. The method needs no large experimental equipments except for a centrifuge, which has a low cost and which is convenient and fast, with short operation time and the possibility of carrying out parallel operations with a large number of samples. The high purity exosomes obtained by the method can meet the demand of large-scale clinical applications.

6 Claims, 4 Drawing Sheets

(51) Int. Cl.
  *C12Q 1/00* (2006.01)
  *B01D 63/08* (2006.01)
  *B01D 63/06* (2006.01)
  *B01D 61/14* (2006.01)
  *B01D 63/16* (2006.01)
  *B01D 69/02* (2006.01)
  *G01N 1/34* (2006.01)
  *G01N 1/40* (2006.01)

(52) U.S. Cl.
  CPC ......... *B01D 63/087* (2013.01); *B01D 63/16* (2013.01); *B01D 69/02* (2013.01); *B01L 3/5021* (2013.01); *C12Q 1/00* (2013.01); *G01N 1/34* (2013.01); *G01N 1/4077* (2013.01); *B01D 2325/02* (2013.01); *B01D 2325/34* (2013.01); *B01L 2200/0684* (2013.01); *B01L 2300/048* (2013.01); *B01L 2300/0681* (2013.01); *G01N 2001/4088* (2013.01)

(56) References Cited

U.S. PATENT DOCUMENTS

| | | | |
|---|---|---|---|
| 9,005,888 B2 | 4/2015 | Antes et al. | |
| 2013/0273544 A1* | 10/2013 | Vlassov | G01N 33/5076 435/6.12 |
| 2016/0074860 A1 | 3/2016 | Mitsuhashi et al. | |
| 2016/0237496 A1* | 8/2016 | Mitsuhashi | C12Q 1/6883 |
| 2018/0066307 A1* | 3/2018 | Ter-Ovanesyan | C12Q 1/6804 |

FOREIGN PATENT DOCUMENTS

| | | |
|---|---|---|
| CN | 102967492 A | 3/2013 |
| CN | 103599574 A | 2/2014 |
| CN | 203754716 U | 8/2014 |
| CN | 203768278 U | 8/2014 |
| CN | 102967492 B | 10/2015 |
| CN | 105319093 A | 2/2016 |
| CN | 105505854 A | 4/2016 |
| CN | 205898536 U | 1/2017 |
| DE | 69406523 T2 | 4/1998 |
| EP | 0651675 A1 | 12/1994 |
| EP | 0651075 A1 | 5/1995 |
| EP | 0651675 B1 | 10/1997 |
| EP | 3052661 | 8/2016 |
| JP | H08501727 A | 2/1996 |
| JP | 3197014 B2 | 8/2001 |
| JP | 5544399 B2 | 7/2014 |
| JP | 2015216906 A | 12/2015 |
| JP | 2016540496 A | 12/2016 |
| TW | 201311340 A | 3/2013 |
| TW | I520772 B | 2/2016 |
| WO | 9427724 A1 | 12/1994 |
| WO | 2013158203 A1 | 10/2013 |
| WO | 2015050891 A2 | 4/2015 |
| WO | 2015050891 A3 | 4/2015 |
| WO | 2015085096 A1 | 6/2015 |
| WO | 2016033695 A1 | 3/2016 |

OTHER PUBLICATIONS

Clotilde Thery, et al., "Isolation and Characterization of Exosomes from Cell Culture Supernatants and Biological Fluids," Current Protocols in Cell Biology 2006.
Hadi Valadi, et al., "Exosome-mediated Transfer of mRNAs and MicroRNAs is a Novel Mechanism of Genetic Exchange Between Cells," Nature Cell Biology, vol. 9, No. 6, Jun. 2007.
Suresh Mathivanan, et al., "Proteomics Analysis of A33 Immunoaffinity-purified Exosomes Released from the Human Colon Tumor Cell Line LIM1215 Reveals a Tissue-specific Protein Signiture," Molecular & Cellular Proteomics 9.2, The American Society for Biochemistry and Molecular Biology, Inc., 2010, pp. 197-208.
Bow J. Tauro, et al., "Comparison of Ultracentrifugation, Density Gradient Seperation, and Immunoaffinity Capture Methods for Isolating Human Colon Cancer Cell Line LIM1863-derived Exosomes," Methods Journal, Jan. 21, 2012, pp. 293-304.
Douglas D. Taylor, et al., "Exosome Isolation for Proteomic Analyses and RNA Profiling," Serum/Plasma Proteomics Methods and Protocols, Methods in Molecular Biology, vol. 728, 2011, pp. 235-246.
Pauline E. Chugh, et al., "Systemically Circulating Viral and Tumor-Derived MicroRNAs in KSHV—Associated Malignancies", PLOS Pathogens, vol. 9, Issue 7, Jul. 2013, pp. 1-22.
Mahmodul Hasan Sohel, et al., "Exosomal and Non-Exosomal Transport of Extra-Cellular MicroRNAs in Follicular Fluid: Implications for Bovine Oocyte Developmental Competence," PLOS One, vol. 8, Issue 11, Nov. 2013, pp. 1-16.
Kadri Rekker, et al., "Comparison of Serum Exosome Isolation Methods for MicroRNA Profiling," Clinical Biochemistry, The Canadian Society of Clinical Chemists, 2013, pp. 135-138.
Richard Wubbolts, et al., "Proteomic and Biochemical Analyses of B Cell-Derived Exosomes," The Journal of Biological Chemistry, vol. 278, No. 13, Mar. 28, 2003 pp. 10963-10972.
Anita Cheruvanky, et al., "Rapid Isolation of Urinary Exosomal Biomarkers Using a Nanomembrane Ultrafiltration Concenrator," Am J Physiol Renal Physiol, vol. 292, 2007, pp. F1658-F1661.
Lamparski G. Henry, et al. "Production and Characterization of Clinical Grade Exosomes Derived from Dendritic Cells," Journal of Immunological Methods 270 (2002) pp. 211-226.
International Search Report and Written Opinion dated Apr. 17, 2017, for corresponding International Application No. PCT/CN2016/097562; International Filing Date: Aug. 31, 2016, consisting of 9-pages.

\* cited by examiner

METHOD FOR EXOSOME SEPARATION AND EXTRACTION BY STACKED CENTRIFUGAL FILTRATION

CROSS-REFERENCE TO RELATED APPLICATIONS

This application is the United States National Stage entry under 35 U.S.C. 371 of PCT/CN2016/097562 filed on Aug. 31, 2016, which in turn claims the priority of Chinese patent application No. 201610595164.2 entitled "Multi-layered Centrifugal Filter for Exosome Extraction" filed on Jul. 26, 2016, both of which are hereby incorporated by reference in their entirety.

FIELD OF THE INVENTION

This invention belongs to the field of molecular biology and clinical examination, particularly relate to a method for exosome separation and extraction by stacked centrifugal filtration.

BACKGROUND OF THE INVENTION

Exosome is a type of extracellular vesicles with the size of 30-150 nm in diameter. They can be produced by most eukaryotic cell types through the fusion of multivesicular bodies (MVBs). These nano-particles can transport a variety of signaling molecules, including proteins, lipids and nucleic acid (mRNAs and miRNAs, etc.). Based on the ligand-receptor recognition, exosomes can be specifically captured by certain target cells that is one of the most important ways in cell-cell communication.

Currently, exosome extraction methods are mainly classified into the following types: ultracentrifugation, polymer or magnetic bead precipitation and ultrafiltration.
  1. Ultracentrifugation is the most widely used method in exosome extraction[1-4]. The centrifugation speed differs from literatures, and the method mainly includes 4 steps: (1) low speed centrifugation (about 300×g) to remove the remaining cells; (2) high speed centrifugation (about 16,500×g) to remove cell debris; (3) large vesicles through removal by filtration with 0.22 μm membrane; (4) exosome precipitation with ultracentrifugation (about 120,000×g). Optionally, sucrose gradient may be used to improve purity of exosomes.

The disadvantages to collect exosome with ultracentrifugation are mainly listed as follows:
  1) The operation is time-consuming: it takes about 8-24 hours to collect exosomes from biological fluid;
  2) Low separation efficiency: it has been proven that the recovery rate of exosomes isolated by ultracentrifuge is about 10%[5]. Relatively large amount of samples are required to obtain sufficient sample for subsequent analyses;
  3) Specific instrument indispensable: the ultracentrifuge needed for extraction is not a conventional laboratory apparatus;
  4) Limitation in parallel operation: the number of samples which can be operated parallel at the same time depends on the centrifuge rotors. In most cases, no more than 6 samples can be run simultaneously.
  2. The polymer precipitation method overcomes some of the disadvantages of the ultracentrifugation. It has been widely used in the field of scientific researches[6-8] with commercial reagents for sale[9,10]. This method is performed by mixing the sample with the polymer solution at a given ratio, followed by incubation for about 30 min. Then the exosomes are pelleted through centrifugation at low speed (~10,000×g), and finally the exosomes can be resuspended in isotonic buffer.

The main disadvantages of the polymer precipitation method are listed as follows:
  1) High cost: taking popular commercial reagents such as ExoQuick-TC from System Biosciences (SBI) as an example, the expenses of reagents in performing isolation is about $30 per sample.
  2) Limitation in subsequent applications: since additional component (polymer solution) was added, the exosomes acquired cannot be directly used in various subsequent applications, e.g. cell culture and transfusion, etc.
  3) Unsuitable for large-volume samples: based on the principle and high cost mentioned above, such method is unsuitable for treatment of large-volume samples.
  3. The magnetic bead precipitation is another popular exosome extraction method[1,11]. This method relies on incubation of the sample with the magnetic beads coupled with specific antibody such as anti-CD63. Exosomes expressing the corresponding antigen can be captured based on the antigen-antibody reaction and precipitated along with the magnetic beads.

Similarly, the magnetic head method has apparent disadvantages:
  1) High cost: special capacity is needed in manufacturing the magnetic beads, and the conjugation of antibodies with the beads further increase the cost of the method.
  2) Only certain subgroup of exosomes can be purified: according to the antigen-antibody reaction, only the subgroup of exosomes presenting specific antigen in the surface can be precipitated. This will theoretically lose other exosomes subtypes.
  3) Unsuitable for large-volume samples: due to its principle and high cost above, the method is unsuitable for treatment of large-volume samples.
  4. Ultrafiltration was performed by some of the researchers in literature for exosome enrichment[12,13]; however, ultracentrifugation will be further performed to further precipitate of the exosomes. Therefore, such a method is not suitable for clinical applications, neither. Notably, there is no exosome extraction method by ultrafiltration which can be used for serum/plasma.

In conclusion, currently, no exosome extraction method can meet the demand of large-scale clinical applications with low cost, being convenient and fast, and can operate with a large number of samples parallelly, especially for serum samples.

REFERENCES

[1] Thery, C., Amigorena, S., Raposo, G., and Clayton, A. Isolation and characterization of exosomes from cell culture supernatants and biological fluids, Curr Protoc Cell Biol Chapter 3, Unit 3 22 (2006). PMID: 18228490.
[2] Valadi, H., Ekstrom, K., Bossios, A., Sjostrand, M., Lee, J. J., and Lotvall, J. O. Exosome-mediated transfer of mRNAs and microRNAs is a novel mechanism of genetic exchange between cells, Nature cell biology 9, 654-9 (2007). PMID: 17486113.
[3] Mathivanan, S., Lim, J. W., Tauro, B. J., Ji, H., Moritz, R. L., and Simpson, R. J. Proteomics analysis of A33 immunoaffinity-purified exosomes released from the human colon tumor cell line LIM1215 reveals a tissue-specific protein signature, Mol Cell Proteomics 9, 197-208 (2010). PMID: 19837982.

[4] Tauro, B. J., Greening, D. W., Mathias, R. A., Ji, H., Mathivanan, S., Scott, A. M., and Simpson, R. J. Comparison of ultracentrifugation, density gradient separation, and immunoaffinity capture methods for isolating human colon cancer cell line LIM1863-derived exosomes, Methods 56, 293-304 (2012). PMID: 22285593.

[5] Taylor, D. D., Zacharias, W., and Gercel-Taylor, C. Exosome isolation for proteomic analyses and RNA profiling, Methods Mol Biol 728, 235-46 (2011). PMID: 21468952.

[6] Chugh, P. E., Sin, S. H., Ozgur, S., Henry, D. H., Menezes, P., Griffith, J., Eron, J. J., Damania, B., and Dittmer, D. P. Systemically circulating viral and tumor-derived microRNAs in KSHV-associated malignancies, PLoS Pathog 9, e1003484 (2013). PMID: 23874201.

[7] Sohel, M. M., Hoelker, M., Noferesti, S. S., Salilew-Wondim, D., Tholen, E., Looft, C., Rings, F., Uddin, M. J., Spencer, T. E., Schellander, K., and Tesfaye, D. Exosomal and Non-Exosomal Transport of Extra-Cellular microRNAs in Follicular Fluid: Implications for Bovine Oocyte Developmental Competence, PLoS One 8, e78505 (2013). PMID: 24223816.

[8] Rekker, K., Saare, M., Roost, A. M., Kubo, A. L., Zarovni, N., Chiesi, A., Salumets, A., and Peters, M. Comparison of serum exosome isolation methods for microRNA profiling, Clin Biochem 47, 135-8 (2014). PMID: 24183884.

[9] Antes, T. J., Kwei, K., and Wu, F., (US, 2015).

[10] Vlassov, A., Li, M., Zeringer, E., and Conrad, R., (WO, 2015).

[11] Wubbolts, R., Leckie, R. S., Veenhuizen, P. T., Schwarzmann, G., Mobius, W., Hoernschemeyer, J., Slot, J. W., Geuze, H. J., and Stoorvogel, W. Proteomic and biochemical analyses of human B cell-derived exosomes. Potential implications for their function and multivesicular body formation, J Biol Chem 278, 10963-72 (2003). PMID: 12519789.

[12] Cheruvanky, A., Zhou, H., Pisitkun, T., Kopp, J. B., Knepper, M. A., Yuen, P. S., and Star, R. A. Rapid isolation of urinary exosomal biomarkers using a nanomembrane ultrafiltration concentrator, American journal of physiology. Renal physiology 292, F1657-61 (2007). PMID: 17229675.

[13] Lamparski, H. G., Metha-Damani, A., Yao, J. Y., Patel, S., Hsu, D. H., Ruegg, C., and Le Pecq, J. B. Production and characterization of clinical grade exosomes derived from dendritic cells, Journal of immunological methods 270, 211-26 (2002). PMID: 12379326.

SUMMARY OF THE INVENTION

The object of the invention is to provide a method for exosome separation and extraction by stacked centrifugal filtration.

The technical solution of the invention is described below.

A stacked centrifugal filtration device for exosome separation and extraction is provided, comprising:

a filter tube comprising a filter membrane at the bottom, a primary support edge provided with an air passage at the top tube opening, and a primary filter tube cavity within the filter tube, an ultrafiltration tube arranged outside of the filter tube, comprising an ultrafiltration membrane at the bottom, a secondary support edge provided with an air passage at the top tube opening, and a secondary filter tube cavity within the ultrafiltration tube and below the filter tube, and a collecting tube arranged outside of the ultrafiltration tube, comprising a collecting tube cavity within the collecting tube and below the ultrafiltration tube, and a cap provided at the top opening of the tube, when it is capped, the primary support edge may be pressed on the secondary support edge, and the secondary support edge may be pressed on the edge of the collecting tube, and the primary filter tube cavity and the secondary filter tube cavity can be connected to the atmosphere through the air passages.

Preferably, the pore size of the filter membrane is not greater than 1 μm.

Preferably, the pore size of the filter membrane is not greater than 0.8 μm.

Preferably, the molecular weight range of the ultrafiltration membrane is from 30 to 100 kDa.

Preferably, both the left and right sides of the ultrafiltration tube wall are planar and inclining towards the middle part; a secondary filter tube with a V-shape cross section cavity which is formed by the two planar walls; at least one window for the ultrafiltration membrane is arranged on one or both side(s) of the planar walls; an ultrafiltration membrane assembly is nested in the ultrafiltration membrane window; the ultrafiltration membrane assembly includes an ultrafiltration membrane fixing plate with an ultrafiltration membrane attached inside; several outflowing holes are arranged at the lower end of the ultrafiltration membrane fixing plate.

Preferably, the collecting tube can be occluded by thread- or snap-cap.

In an embodiment of the invention, a kit for exosome separation and extraction is provided comprising any one of the above stacked centrifugal filtration devices, incubation buffer and protease K.

Preferably, the incubation buffer solution comprises the following components: DPBS, 60-240 mM Tris, 60-180 mM EDTA, and its pH is 7-7.5.

DPBS, i.e. Dulbecco's phosphate-buffered saline, is a balanced saline solution used to maintain activities of mammal cells for a short period of time. It can maintain the structural and physiological integrity of in vitro cells for a limited time. Preferably, DPBS includes the following components: KCl 200 mg/L; $KH_2PO_4$ 200 mg/L; NaCl 8 g/L; $Na_2HPO_4 \cdot 7H_2O$ 2.16 g/L.

Preferably, Tris can be added in solid form or in solution form prepared by its soluble salts.

Preferably, EDTA can be added in solid form or in solution form prepared by its soluble salts.

Preferably, the pH of the incubation buffer solution is adjusted by HCl or NaOH.

In an embodiment of the invention, a method for exosome separation and extraction is provided comprising the following steps:

1) adding the incubation buffer into the sample to be tested, the volume of the incubation buffer should be 0.1-5 times of that of the sample, and appropriate amount of protease K is added in at the same time, mixing thoroughly and incubating at room temperature;

2) transferring all liquid in step 1) into the filter tube of the stacked centrifugal filtration device mentioned above, positioning the stacked centrifugal filtration device in a centrifuge for centrifugation, mixing thoroughly, and collecting the retentate in the ultrafiltration tube to obtain the exosomes.

Preferably, the incubation buffer comprises the following components: DPBS, 60-240 mM Tris, 60-180 mM EDTA, and its pH is 7-7.5.

Preferably, the incubation buffer comprises the following components: DPBS, 80-220 mM Tris, 80-160 mM EDTA, and its pH is 7-7.5.

Preferably, in step 1), an appropriate amount of protease K is added to make the concentration of 0.2 mg/mL to 2.0 mg/mL. When the concentration of the protease K solution is 5-40 mg/mL, the amount of protease K added is 0.005-0.4 times of the sample volume.

Preferably, in step 1), after addition of protease K, the mixture should be incubated at room temperature for 8-20 min.

Preferably, DPBS includes the following components: KCl 200 mg/L; $KH_2PO_4$ 200 mg/L; NaCl 8 g/L; $Na_2HPO_4 \cdot 7H_2O$ 2.16 g/L.

Preferably, for centrifugation in step 2), the centrifugal force should not exceed 5,000×g, and the centrifugation time is 10-30 min.

Preferably, if an increased purity of exosomes is required, then after centrifugation in step 2), an appropriate amount of DBPS may be added into the filter tube, followed by centrifugation again and mixing thoroughly, and collecting the retentate in the ultrafiltration tube to obtain the exosomes.

The advantageous effects of the invention are for example:

Compared with the ultracentrifugation method:

a) equivalent purity of the exosomes obtained by both the ultracentrifugation and the method of the present invention;

b) operation time of the invention can be reduced to 30 min;

c) all processes can be performed at room temperature, no need for refrigerating system;

d) the method of the invention can be performed in any laboratory equipped with a small table-top centrifuge, and no other experimental apparatus is needed;

e) depending on the type of the centrifugal rotor, multiple samples can be treated parallelly with the method of the invention. For example, up to 24 samples can be treated parallelly with the rotor equipped by a common small table-top centrifuge in laboratories.

Compared with the polymer precipitation method:

a) equivalent purity of the exosomes obtained by both the polymer precipitation and the method of the present invention;

b) lower cost of the consumables used by the method of the invention;

c) for subsequent applications, no additional treatment is needed by using the exosomes obtain from this invention.

Compared with the magnetic bead method:

a) lower cost of the consumables used by the method of the invention;

b) all sub-groups of exosomes in the sample can be recovered by using this invention.

DETAILED DESCRIPTION OF THE EMBODIMENTS

The reagent formulations used in the invention comprise:

DPBS: KCl 200 mg/L; $KH_2PO_4$ 200 mg/L; NaCl 8 g/L; $Na_2HPO_4 \cdot 7H_2O$ 2.16 g/L;

Incubation buffer: DPBS+60-240 mM TrisHCl+60-180 mM EDTA, pH=7.2;

Protease K stock solution: 5-40 mg/mL protease K aqueous solution.

Reagents used in the examples are prepared according to the formulations.

The method of the invention comprises the following steps:

1) adding the incubation buffer into the sample to be tested with 0.1-5 times in volume, and adding protease K stock solution with 0.005-0.4 times in volume of the sample, mixing thoroughly and incubating at room temperature for 8-15 min;

2) transferring the mixture in step 1) into the filter tube of the stacked centrifugal filtration device, followed by centrifugation; and the retentate containing purified exosomes is thoroughly mixed and collected in the ultrafiltration tube.

Preferably, if an increased purity of the exosomes is required, DBPS may be added into the ultrafiltration tube for centrifugation at 3,000×g for 10 min to wash and remove certain soluble proteins; one more wash is allowed.

Preferably, an exosome solution, which can be used for subsequent treatment, is obtained after well mixing and collection of the retentate.

The invention is further illustrated in combination with detailed embodiments below. However, the invention is not limited to these embodiments.

Figure 1:
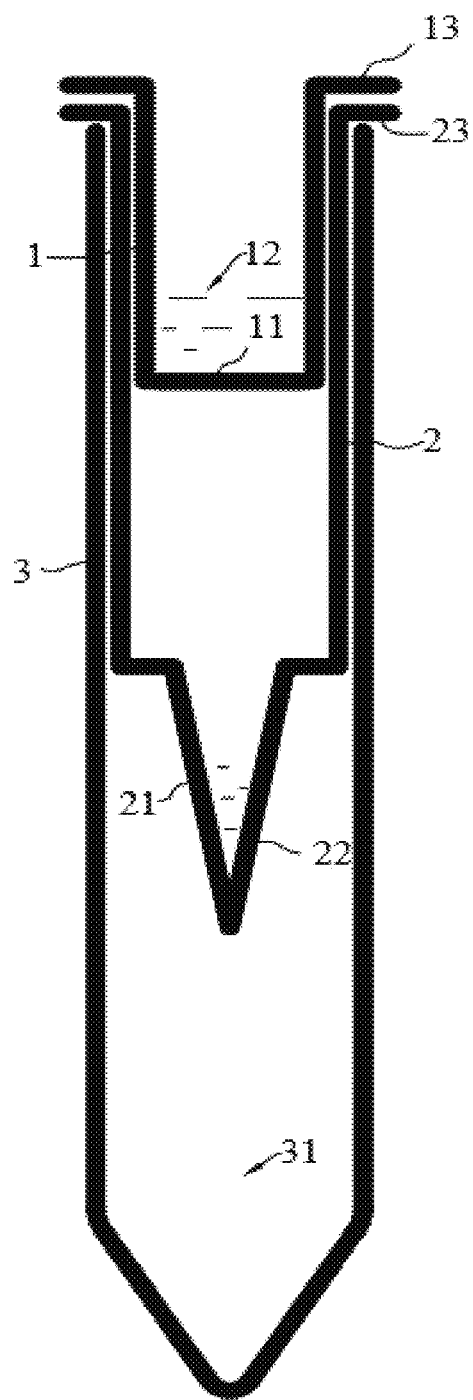
FIG. 1 shows the stacked centrifugal filtration device of the invention.

Example 1. A Stacked Centrifugal Filtration Device for Exosome Separation and Extraction An embodiment of the invention provides a stacked centrifugal filtration device for exosome separation and extraction (as shown in FIG. 1), comprising:

a filter tube 1 comprising a filter membrane 11 at the bottom, a first support edge 13 provided with an air passage at the top tube opening, and a first filter tube cavity 12 within the filter tube, an ultrafiltration tube 2 arranged outside of the filter tube 1, comprising an ultrafiltration membrane 21 at the bottom, a second support edge 23 provided with an air passage at the top tube opening, and a second filter tube cavity 22 within the ultrafiltration tube 2 and below the filter tube 1, and a waste liquid collecting tube 3 arranged outside of the ultrafiltration tube 2, which matches the centrifuge device, comprising a waste liquid collecting tube cavity 31 within the waste liquid collecting tube 3 and below the ultrafiltration tube 2, and a cap provided at the top tube opening of the waste liquid collecting tube 3 through threaded connection or snap fitting connection, when it is capped, the first support edge 13 may be pressed on the second support edge 23, and the second support edge 23 may be pressed on the top tube opening of the waste liquid collecting tube 3, and meanwhile, the first filter tube cavity 12 and the second filter tube cavity 22 are in communication with the external environment through the air passages.

Both the left and right sides of the ultrafiltration tube wall 2 below the filter tube 1 are planar and inclining towards the middle part. A second filter tube cavity 22 with a V-shape cross section is formed between the two planar tube walls. Scale is provided on the outside wall of the second filter tube cavity 22. An ultrafiltration membrane window is arranged on at least one of the planar tube walls. An ultrafiltration membrane assembly is nested in the ultrafiltration membrane window. The ultrafiltration membrane assembly includes an ultrafiltration membrane fixing plate and an ultrafiltration membrane 21 attached on the inner side of the ultrafiltration membrane fixing plate. Several outflowing holes are arranged at the lower end of the ultrafiltration membrane fixing plate.

Preferably, the pore size of the filter membrane is not greater than 1 μm.

Preferably, the pore size of the filter membrane is not greater than 0.8 μm.

Preferably, the pore size of the filter membrane is 0.22 μm.

The common pore size of the filter membrane is 0.1-100 μm. Common interferents in serum are high abundance proteins and microvesicles (MVs). After the pretreatment under buffer solution and protease K of the invention, a large proportion of high abundance proteins is digested into fragments by protease K. The diameter of a MV is about 200-1,000 nm. The interference from most MVs can be eliminated with a 0.22 μm filter membrane.

Preferably, the ultrafiltration membrane is an ultrafiltration membrane with a molecular weight range of 30-100 kDa for particles.

The MVs are retained in the filter tube by the filter membrane. The main contaminations entering the second filter tube cavity are polypeptide fragments resulted from enzyme digestion of high abundance proteins by protease K. In the invention, most of the polypeptide fragments after treatment are linear molecules with a molecular weight of 5-10 kDa. Therefore, an ultrafiltration membrane with a range molecular weight of greater than 30 kDa is chosen to filter out the polypeptide fragments. At the same time, since the pore size of the ultrafiltration membrane within this range is much smaller than the diameter of the exosomes, the exosomes are retained in the second filter tube cavity.

Using the stacked centrifugal filtration device for exosome separation and extraction of the invention, when the serum sample to be tested is added into the filter tube, the serum sample flows through the filter membrane 11 at the bottom of the filter tube 1 under centrifugal force. A common filter membrane 11 is a micropore filter membrane with a pore size not greater than 1 μm, preferably 0.22 μm. Most MVs are retained in the filter tube 1. The exosomes, soluble proteins, enzymatic hydrolyzed fragments of high abundance proteins enter the ultrafiltration tube 2 through this filter membrane. Due to the ultrafiltration membrane 21 at the lower part of the tube wall of the ultrafiltration tube 2 and the second filter tube cavity 22 at the bottom, during centrifugation, soluble fractions, enzymatic hydrolyzed fragments of high abundance proteins and smaller particles permeate through the ultrafiltration membrane 21 on the side wall and enter the waste liquid collecting tube 3. Due to the second filter tube cavity 22 at the bottom of the ultrafiltration tube 2, part of the liquid is retained during the centrifugation process, and the exosomes are trapped in this liquid. After centrifugation, the ultrafiltration tube 2 is taken out to mix the liquid well in the retaining cavity with a pipette. The retained liquid is collected as the final product, exosome solution.

Example 2. A Kit for Exosome Separation and Extraction

The kit includes the following components:
1) a stacked centrifugal filtration device as described in example 1.
2) an incubation buffer, comprising the following components: DPBS, 60-240 mM TrisHCl buffer, 60-180 mM EDTA, and its pH is 7-7.5.
3) a protease K stock solution with a concentration of 5-40 mg/mL.
4) DPBS: KCl 200 mg/L; $KH_2PO_4$ 200 mg/L; NaCl 8 g/L; $Na_2HPO_4 \cdot 7H_2O$ 2.16 g/L.

Example 3. A Method for Exosome Separation and Extraction

Exosomes are separated and extracted using the kit of Example 2.

The following steps are performed:
1) adding the incubation buffer with a volume 0.5 times of the sample to be tested, and adding protease K stock solution with a volume of 0.05 times, mixing thoroughly and incubating at room temperature for 8-15 min;
2) transferring the sample treated in step 1) into the filter tube of the stacked centrifugal filtration device (as shown in FIG. 1) to carry out centrifugation, then mix thoroughly, and collect the retained liquid in the ultrafiltration tube.

Preferably, if an increased purity of the exosomes is required, DBPS may be added into the ultrafiltration tube to carry out centrifugation at 3,000×g for 10 min to wash and remove certain soluble proteins; one more wash is allowed.

Preferably, the retained liquid is mixed well and collected as the exosome solution which can be used for subsequent treatment.

The method of the invention and the extraction method of prior art or the commercial reagent extraction method are compared below.

Comparative Experiment Between the Method of the Invention and Commercial Reagent Extraction Method Currently, reagents for exosome extraction are mainly ExoQuick series from SBI and Total Exosome Isolation Reagent series from ThermoFisher. Both methods work with similar principle and have an equivalent extraction purity. Here compared is the extraction effect of the product suitable for serum with reagents from ThermoFisher vs. the present invention (Example 3) on a same serum sample.

The commercial reagent extraction method includes the following steps:
(1) drawing 200 μL serum into a new EP tube;
(2) adding 40 μL Total Exosome Isolation Reagent (from Serum) and mixing thoroughly;
(3) incubating at 4° C. for 30 min;
(4) taking out the above mixture for centrifugation at 10,000×g for 10 min;
(5) removing the supernatant, and adding 20 μL DPBS to resuspend the precipitation thus obtaining exosome solution.

Figure 2:
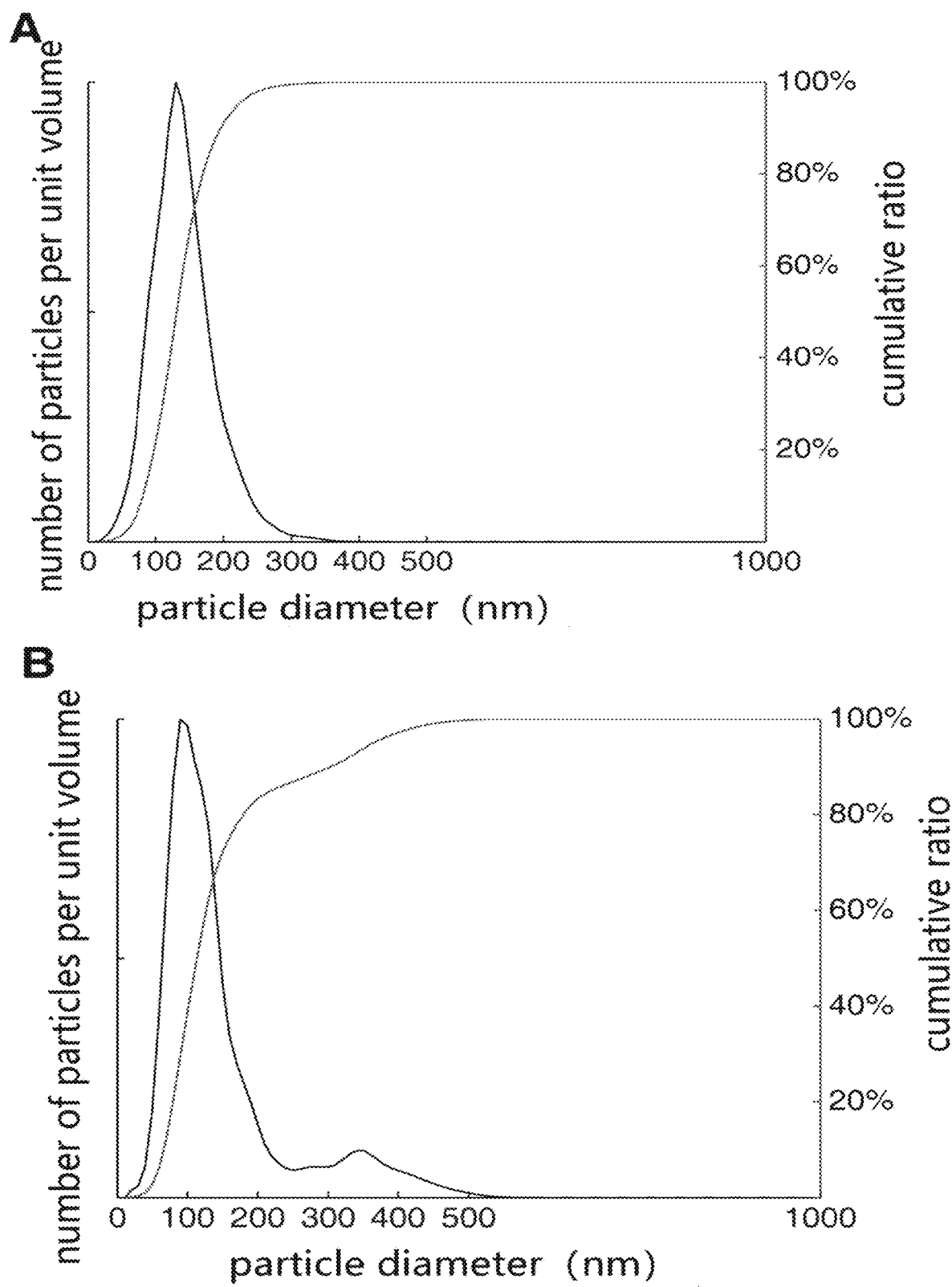
FIG. 2 shows the purity testing results of the exosomes.

The purity of the exosomes obtained above and the exosomes obtained in Example 3 are determined and the results are given in FIG. 2.

In FIG. 2, A is the result of exosomes extracted with commercial reagents, while B is the purity result of exosomes extracted with the method of the invention. As shown in FIG. 2, the purity of the exosomes extracted with the method of the invention is equivalent to that of commercial reagents. At the same time, the invention has a shorter operation time than that with commercial reagents and has advantages in cost.

Comparative Experiment of Extraction Systems

Exosome extraction effects of exosome kits with minimum component concentration, maximum component concentration and concentration of the invention are compared.

The specific extraction method is as follows:
Incubation buffer of the invention (DPBS+90 mM TrisHCl+90 mM EDTA, pH=7.2); high concentration incubation buffer (DPBS+250 mM TrisHCl+200 mM EDTA, pH=7.2) and low concentration incubation buffer (DPBS+50 mM TrisHCl+50 mM EDTA, pH=7.2) are prepared respectively.

Protease K stock solution (20 mg/mL), low concentration protease K stock solution (5 mg/mL) and high concentration protease K stock solution (40 mg/mL) are prepared.

200 μL serum is added into each of 3 new EP tubes. According to different concentrations of reagents added, the experiment is divided into the following three testing groups for comparison, wherein: in the high concentration group, 100 μL high concentration incubation buffer and 10 μL high concentration protease K stock solution are used; in the low concentration group, 100 μL low concentration incubation buffer and 10 μL low concentration protease K stock solution are used; and in the invention group, 100 μL incubation buffer and 10 μL protease K stock solution of the invention are used.

Figure 3:
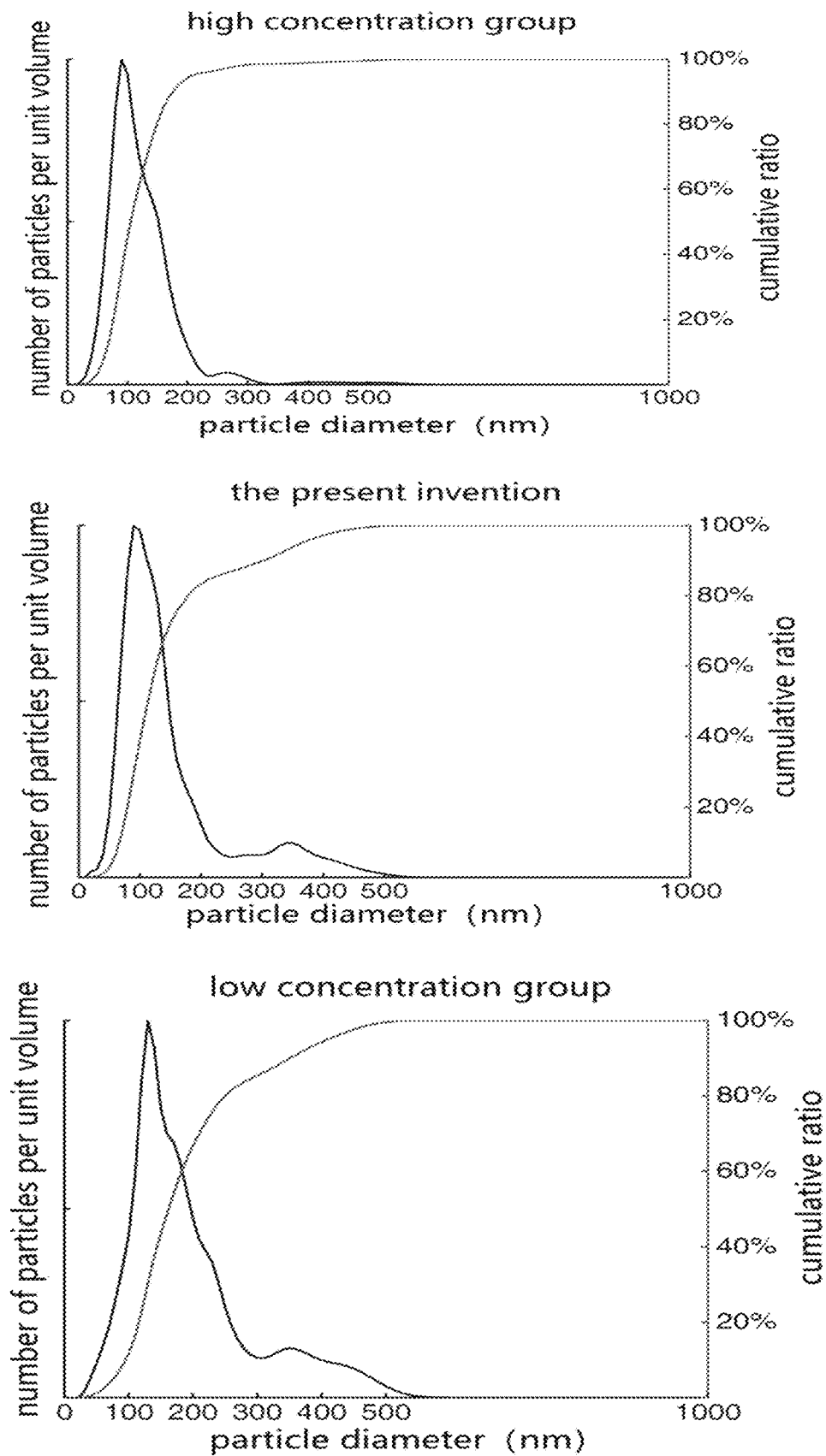
FIG. 3 shows the purity testing results of the exosomes.

The above mixtures are incubated at room temperature for 10 min. Then the mixtures are transferred into the filter tube of the stacked centrifugal filtration device for centrifugation at 3,000×g for 10 min. Then, the liquid retained in the ultrafiltration tube is collected for determination of the purity of the exosomes. The purity testing results are given in FIG. 3.

As shown by the exosome purity determination results (FIG. 3), the exosome concentration of the invention group is equivalent to that of the low concentration group, with $2.73 \times 10^8$ particles/mL and $2.04 \times 10^8$ particles/mL, respectively. However, the particle diameters of the exosomes obtained by the invention are mainly (>80%) within the range of below 200 nm, while only about 60% of the products obtained by the low concentration group have a particle diameter below 200 nm with more large particles present.

At the same time, the particle diameter distribution of the invention is equivalent to that of the high concentration group. However, in terms of extracted exosome concentration, the total extracted particle concentration of the high concentration group ($1.20 \times 10^8$ particles/mL) is only about 50% of that of the invention ($2.73 \times 10^8$ particles/mL).

In conclusion, the exosomes obtained with the buffer and protease K at working concentrations according to the invention are the best.

TEM Measurement of Exosomes

For the exosomes extracted in Example 3 of the invention from the plasma sample, the retentate is washed twice with 2 mL DPBS, and then centrifuged to collect the retained liquid in the ultrafiltration tube. The retained liquid is immobilized on a copper net for staining, followed by measurement using TEM. The result is shown in FIG. 4.

Figure 4:
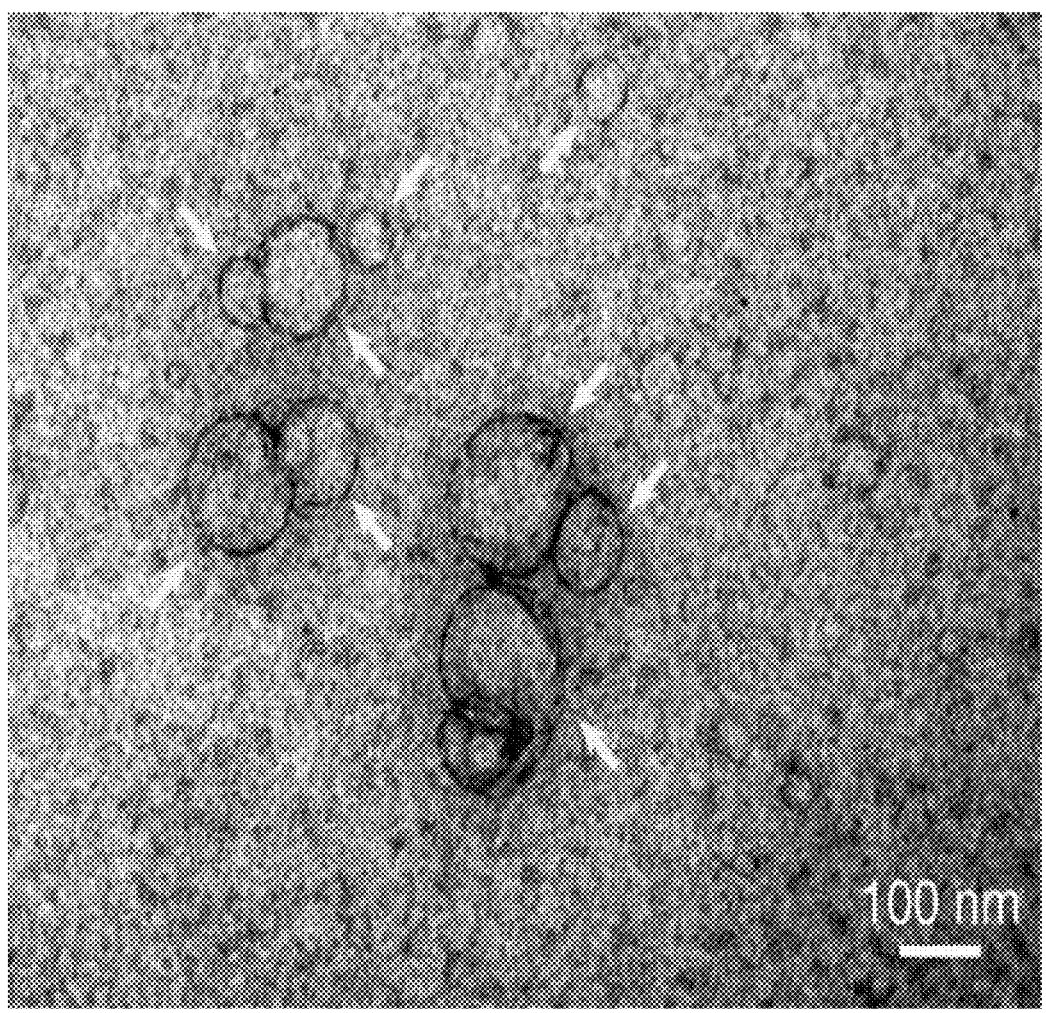
FIG. 4 shows an electron microscope photo of the exosomes.

As shown in FIG. 4, the exosomes extracted from plasma by the invention have an integrated envelope structure with a diameter between 30-150 nm, which is in consistent with the features reported by literatures.

The above embodiments are preferred embodiments of the invention. The invention is not limited by the above examples. Various changes, modifications, substitutes, combinations and simplifications made without departing from the scope of the invention are considered as equivalent substitutes of the invention and are within the protection scope of the invention.

What is claimed is:

1. A method for exosome separation and extraction, comprising:

1) adding an incubation buffer into a sample to be tested, the volume of the incubation buffer being 0.1-5 times that of the sample, and adding an amount of protease K to make the final concentration of protease K be 0.2 mg/mL-2.0 mg/mL at the same time, mixing and incubating at room temperature;

2) transferring all liquid in step 1) into a filter tube of a stacked centrifugal filtration device for exosome separation and extraction, positioning the stacked centrifugal filtration device in a centrifuge for centrifugation, and collecting the retentate in an ultrafiltration tube to obtain the exosomes;

wherein the stacked centrifugal filtration device for exosome separation and extraction comprises:

a filter tube comprising a filter membrane at the bottom of the filter tube, a primary support edge provided with a first air passage at a top tube opening of the filter tube, and a primary filter tube cavity within the filter tube, an ultrafiltration tube arranged outside of the filter tube comprising:
an ultrafiltration membrane at the bottom of the ultrafiltration tube,
a secondary support edge provided with a second air passage at a top tube opening of the ultrafiltration tube, and a secondary filter tube cavity within the ultrafiltration tube and below the filter tube, a collecting tube arranged outside of the ultrafiltration tube comprising:
a collecting tube cavity within the collecting tube and below the ultrafiltration tube, and
a cap provided at the top of the collecting tube, when the stacked centrifugal filtration device is capped, the primary support edge is pressed on the secondary support edge, the secondary support edge is pressed on a top tube opening of the collecting tube, and the primary filter tube cavity and the secondary filter tube cavity are connected to the atmosphere through the first and second air passages; and wherein: both left and right sides of the ultrafiltration tube wall are planar and inclining towards a middle part;
a secondary filter tube cavity with a V-shape cross section is formed by the two planar walls; and
at least one window for the ultrafiltration membrane is arranged on one or both sides of the two planar walls.

2. The method according to claim 1, wherein the incubation buffer comprises: DPBS, 60-240 mM Tris, and 60-180 mM EDTA, and a pH of the incubation buffer is 7-7.5.

3. The method according to claim 1, wherein, for the centrifugation in step 2), a centrifugal force does not exceed 5,000×g, and the centrifugation lasts for 10-30 min.

4. The method according to claim 1, wherein a pore size of the filter membrane is not greater than 1 μm.

5. The method according to claim 1, wherein a molecular weight range of the ultrafiltration membrane is from 30 to 100 kDa.

6. The method according to claim 1, wherein:
an ultrafiltration membrane assembly is nested in the ultrafiltration membrane window;
the ultrafiltration membrane assembly includes an ultrafiltration membrane fixing plate with the ultrafiltration membrane attached on an inner side of the ultrafiltration membrane fixing plate; and
several outflowing holes are arranged at a lower end of the ultrafiltration membrane fixing plate.

* * * * *